United States Patent
Luehrs et al.

(10) Patent No.: US 9,346,864 B2
(45) Date of Patent: May 24, 2016

(54) DEVICE AND METHOD FOR PRODUCTION AND ANALYSIS OF PRIONS

(75) Inventors: Thorsten Luehrs, Braunschweig (DE); Felix Deluweit, Neuwied (DE)

(73) Assignee: SeNostic GmbH, Braunschweig (DE)

( * ) Notice: Subject to any disclaimer, the term of this patent is extended or adjusted under 35 U.S.C. 154(b) by 134 days.

(21) Appl. No.: 13/985,800

(22) PCT Filed: Feb. 15, 2012

(86) PCT No.: PCT/EP2012/052634
§ 371 (c)(1),
(2), (4) Date: Oct. 22, 2013

(87) PCT Pub. No.: WO2012/110570
PCT Pub. Date: Aug. 23, 2012

(65) Prior Publication Data
US 2014/0046025 A1  Feb. 13, 2014

(30) Foreign Application Priority Data

Feb. 16, 2011  (EP) .................................. 11154710

(51) Int. Cl.
*G01N 33/00* (2006.01)
*C07K 14/47* (2006.01)
(Continued)

(52) U.S. Cl.
CPC ................. *C07K 14/47* (2013.01); *B01F 7/008* (2013.01); *B01F 7/00541* (2013.01); *B01F 11/0258* (2013.01); *B01F 13/0836* (2013.01);
(Continued)

(58) Field of Classification Search
CPC ................ B01F 7/169; B01F 7/00216; G01N 2800/2828
See application file for complete search history.

(56) References Cited

U.S. PATENT DOCUMENTS

| 4,536,092 A | 8/1985 | Kedem |
| 2003/0078227 A1 | 4/2003 | Greenleaf et al. |

(Continued)

FOREIGN PATENT DOCUMENTS

| EP | 1 510 246 B1 | 4/2008 |
| EP | 2 280 028 | 2/2011 |

(Continued)

OTHER PUBLICATIONS

Atarashi, Ryuichiro et. al., "Simplified ultrasensitive prion detection by recombinant PrP conversion with shaking", *Nature Methods*, vol. 5, No. 3, Mar. 2008, pp. 211-212.

(Continued)

*Primary Examiner* — Erik B Crawford
(74) *Attorney, Agent, or Firm* — Greer, Burns & Crain, Ltd.

(57) ABSTRACT

The invention provides a method for producing prion protein having an aggregated conformation by contacting native conformation prion protein with aggregated conformation prion protein in a liquid preparation and subjecting this to at least one cycle or to a number of cycles of application of shear-force for fragmenting aggregates of prion protein, wherein the shear-force applied is precisely controlled. In addition to this process for amplification of aggregated state prion protein from native conformation prion protein, the invention relates to the aggregated state prion protein obtained by the amplification process, which aggregated state prion protein has one conformation, which is e.g. identical within one batch and reproducible between batches, e.g. as detectable by proteinase resistance in a Western blot.

6 Claims, 10 Drawing Sheets

Figure 1:
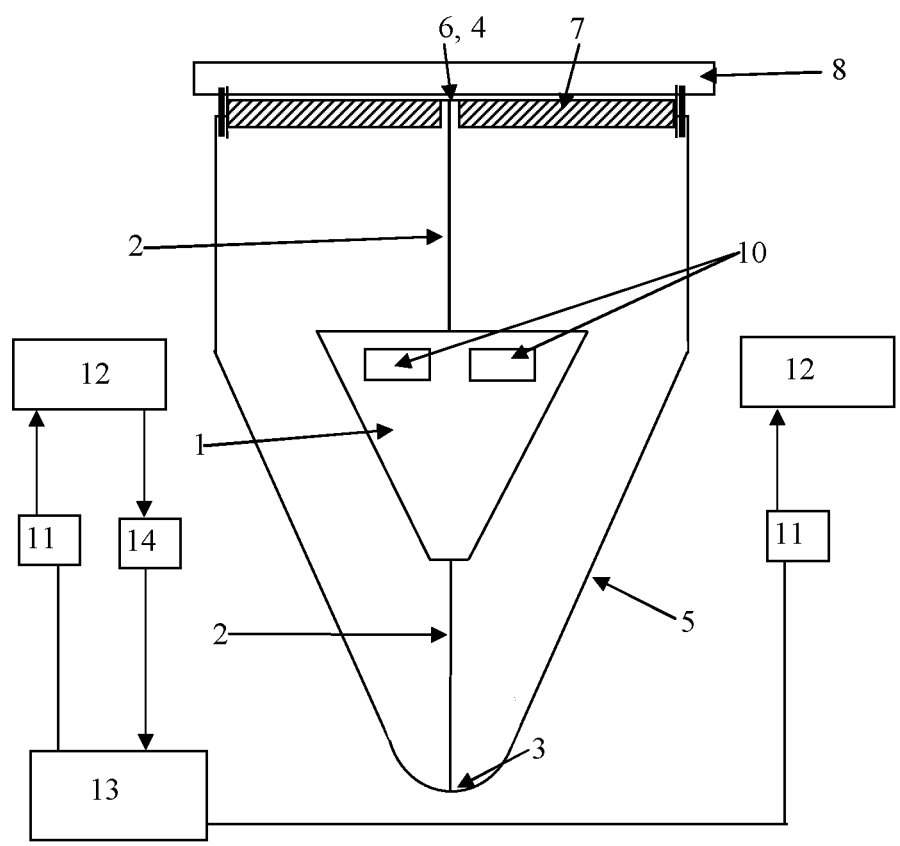

(51) Int. Cl.
  *B01F 7/00* (2006.01)
  *B01F 11/02* (2006.01)
  *B01F 13/08* (2006.01)
  *B01F 15/00* (2006.01)

(52) U.S. Cl.
  CPC ....... *B01F13/0845* (2013.01); *B01F 15/00006* (2013.01); *B01F 15/0072* (2013.01); *B01F 15/00389* (2013.01); *B01F 15/00707* (2013.01); *B01F 2215/0427* (2013.01); *B01F 2215/0431* (2013.01); *B01F 2215/0454* (2013.01); *B01F 2215/0477* (2013.01); *B01F 2215/0481* (2013.01)

(56) References Cited

U.S. PATENT DOCUMENTS

| | | |
|---|---|---|
| 2005/0150830 A1 | 7/2005 | Laugharn, Jr. et al. |
| 2005/0287670 A1 | 12/2005 | Gulliver et al. |
| 2006/0263767 A1 | 11/2006 | Castrillon et al. |
| 2008/0021327 A1 | 1/2008 | El-Bialy et al. |
| 2009/0047696 A1 | 2/2009 | Caughey et al. |

FOREIGN PATENT DOCUMENTS

| | | |
|---|---|---|
| JP | 63-112974 | 5/1988 |
| WO | WO 01-46714 | 6/2001 |

OTHER PUBLICATIONS

Saborio, Gabriela, et. al., "Sensitive detection of pathological prior protein by cyclic amplification of protein misfolding", Nature, vol. 411, Jun. 14, 2001, pp. 810-813.

Castilla, Joaquin, et al., "Detection of prions in blood", Nature Medicine, vol. 11, No. 9, (Sep. 2005), pp. 982-985.

Castilla, Joaquin, et al., "Protein Misfolding Cyclic Amplification for Diagnosis and Prion Propagation Studies", Methods in Enzymology, vol. 412, (2006), pp. 3-21.

European Search Report Dated Jul. 9, 2015 for European Application No. EP 12703832.A.

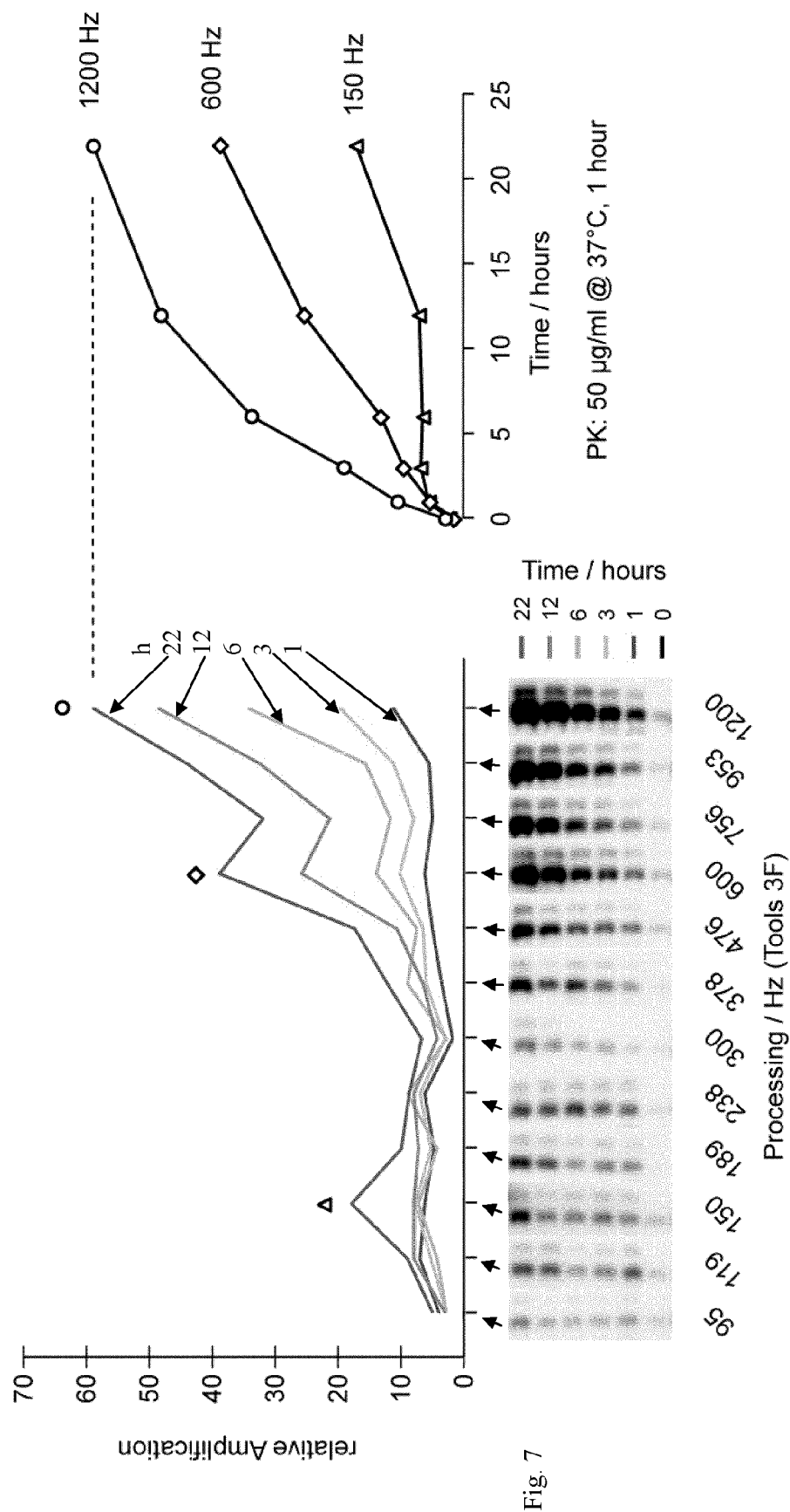

Fig. 12
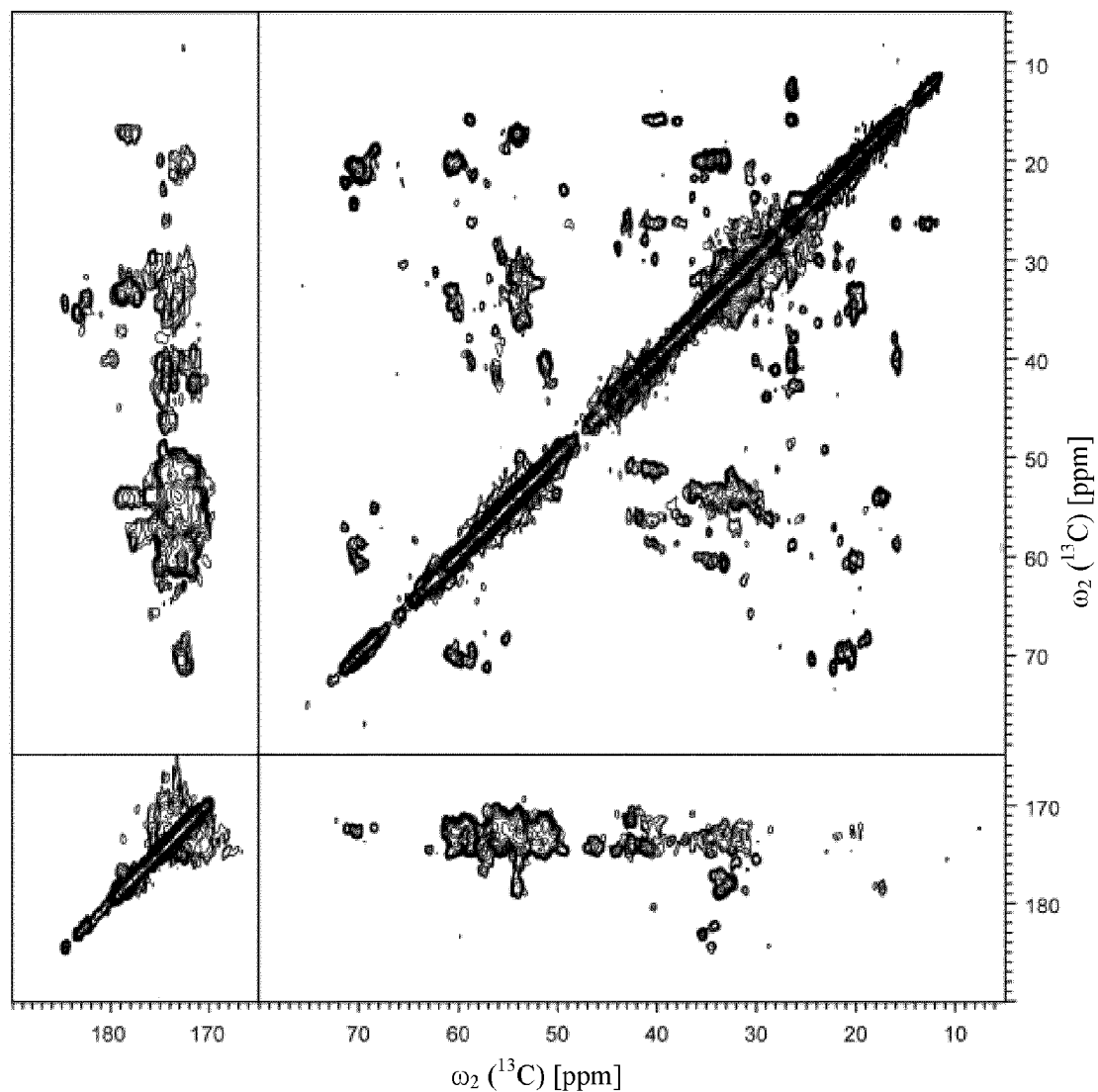
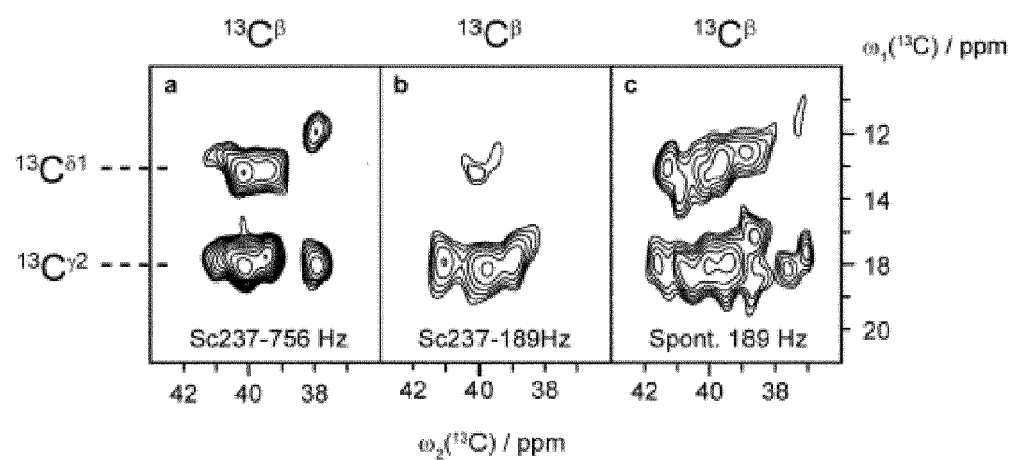

Fig. 13
Fig. 14
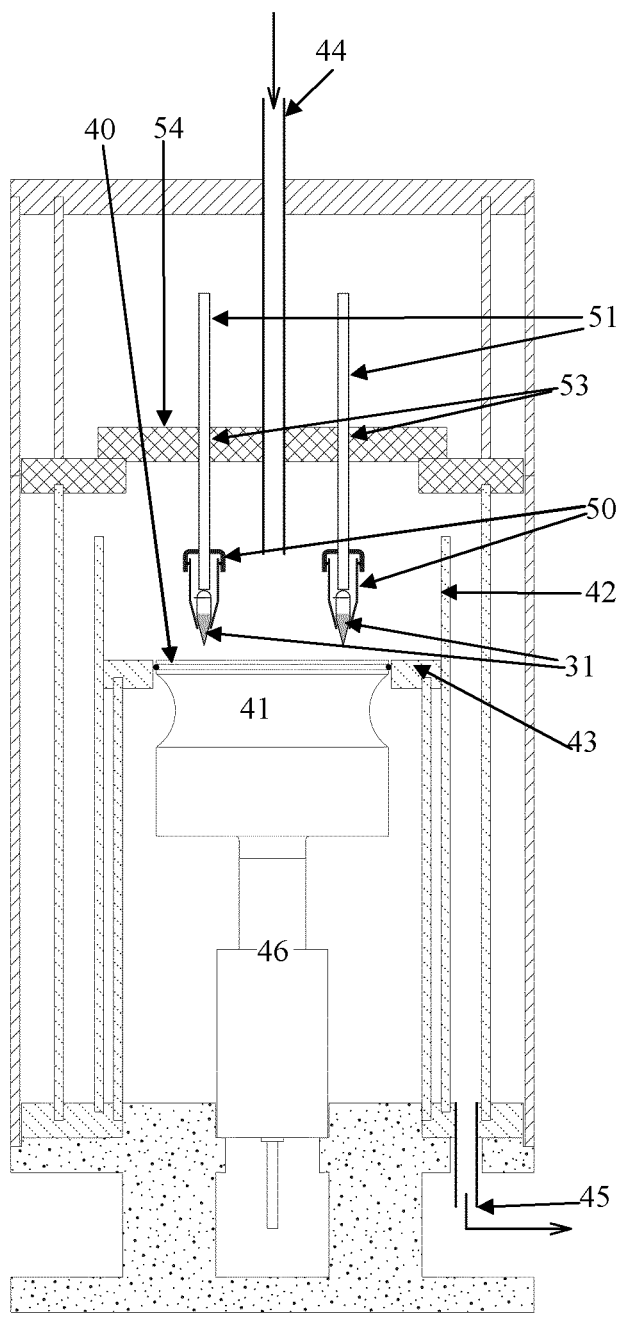
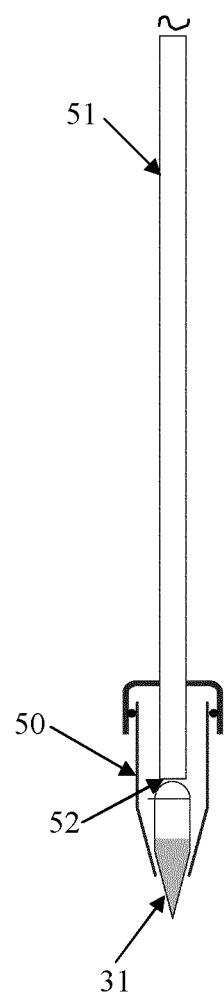

DEVICE AND METHOD FOR PRODUCTION AND ANALYSIS OF PRIONS

The present invention relates to a device and a method using the device for the production of specific conformations of prion particles or of other proteins which in a specific confirmation are associated with the amyloid-like deposits. Further, the invention relates to a preparation of peptides, the amino acid sequence of which contains or consists of the amino acid sequence of a prion or of another peptide forming amyloid-like deposits, the preparation being characterized by an essentially uniform conformation of the peptides. The amino acid sequence of the prion protein can have non-amino acid groups, e.g. saccharide substituents and/or lipid substituents. Further, the invention relates to a process for the analysis of compounds, comprising the step of contacting peptides having the sequence of a prion protein or of a peptide forming amyloid-like deposits in an essentially homogenous conformation, preferably produced by the method according to the invention, with at least one compound, by detecting an interaction of the compound with the peptide, which interaction can e.g. be an association of the compound to the peptide. In this method of analysis, the peptides have the same amino acid sequence and the same conformation, e.g. the conformation of the aggregated state. Generally, the terms prion protein and polypeptide or peptide forming amyloid-like deposits can be used interchangeably, preferably referring to peptides of natural amino acid sequence, which protein or peptides can change their conformation to an aggregated state conformation, e.g. in the presence of one misfolded or aggregated state peptide of the same or of another prion protein amino acid sequence. In the aggregated state conformation of the prion protein, the amyloid-like aggregate forms plaques, e.g. plaques as occurring in amyloid-like plaque forming disease in brain tissue. Aggregated conformation prion protein, e.g. produced by the process of the invention, can also be termed a proteopathic seed when having biological activity, e.g. infectivity in a mammalian species. Exemplary prion proteins are the proteins which in their aggregated state conformation cause or are present in scrapie in sheep (prion protein), bovine spongiform encephalitis in cattle (prion protein), chronic wasting disease in deer and elk (prion protein), and Creutzfeld-Jacob disease, Gerstmann-Sträussler-Scheinker syndrome (prion protein), fatal familial insomnia in humans (prion protein), Alzheimer (beta amyloid), Parkinson (alpha-synuclein), diabetes mellitus type 2 (amylin), chorea Huntington (huntingtin), medullary carcinoma of the thyroid (calcitonin), cardiac arrhythmias, isolated atrial amyloidosis (atrial natriuretic factor), atherosclerosis (apolipoprotein A), rheumatoid arthritis (serum amyloid A), aortic medial amyloid (medin), prolactinomas (prolactin), familial amyloid polyneuropathy (transthyretin), hereditary non-neuropathic systemic amyloidosis (lysozyme), dialysis related amyloidosis (beta-2-microglobulin), Finnish amyloidosis (gelsolin), lattice corneal dystrophy (keratoepithelin), cerebral amyloid angiopathy (beta-amyloid), also of the Icelandic type (cystatin), systemic AL amyloidosis (immunoglobulin light chain AL), sporadic inclusion body myositis (S-IBM), tauopathies involving the agglomeration of tau protein. The amino acid sequence of the prion protein used in the process of the invention can optionally have an added synthetic or natural amino acid section, e.g. a detectable tag.

STATE OF THE ART

Castilla et al. in Methods in Enzymology 3-21 (2006) describe a protein misfolding cyclic amplification process, which includes contacting native conformation prion protein with a minute quantity of misfolded protein, which is assumed to represent the abnormal, disease-associated conformation with intermittent fractionation of generated aggregates by sonication. Analysis of samples was performed by digestion of an aliquot using Proteinase K followed by immuno-blotting with an anti-prion protein antibody in a Western blot, wherein disease-associated, abnormal conformation is detected as protease-resistant peptide sections, which are not observed in the native peptide.

Saborio et al in Nature 810-813 (2001) describe an in vitro process for amplification of infectious prion protein in the aggregated conformation, wherein native conformation prion protein is contacted with prion protein in an aggregated state, which results in the growth of aggregates comprising both native conformation and aggregated conformation prion proteins, followed by sonication in order to disrupt the larger aggregates and a resting phase, which process is performed in cycles. Aggregation of native conformation prion protein with aggregated conformation prion protein results in an increase in aggregated conformation protein, which is caused by a conformation change of native conformation to the aggregated conformation. Sonication results in the fragmentation of the aggregate into an increased number of aggregated conformation prion protein, which in a subsequent resting phase cause further native conformation prion protein to change its conformation to the aggregated state. Analysis of the conversion of the native conformation to the aggregated conformation of prion protein was by digestion with Proteinase K, followed by immuno-blotting with an anti-prion protein antibody in a Western blot. Sonication was done by immersing the ultrasound tip into a sample at a power setting of 40%, repeating for 50-40 cycles of sonication (five pulses, 1 second each), with intermittent incubation times for 1 hour at 37° C. with agitation.

Castilla et al in Nature Medicine 982-985 (2005) developed a method of Saborio et al further and describe the amplification of aggregated conformation prion protein by contacting brain homogenate containing native conformation prion protein with brain homogenate containing scrapie-associated prion protein, using 20 μL samples that were subjected to multiple cycles of sonication and incubation. Detection of aggregated conformation prion protein was by Western blotting of brain homogenate samples after digestion with Proteinase K.

Atarashi et al, Nature Methods 211, 212 (2008) describe the amplification of the aggregated conformation by contacting native conformation prion protein with a brain homogenate containing aggregated conformation prion protein, which could be detected in Western blots as protease resistant forms, by periodic shaking instead of subjecting the samples to periodic sonication. The native conformation prion protein could be produced by bacterial expression. For promotion of the forming of Proteinsase K resistant prion protein, i.e. prion protein in the aggregated state, 0.05-0.1% SDS and 0.05-0.1% Triton X100 was found most effective for amplification of the aggregated conformation of prion protein in native conformation prion protein.

US2006/0263767 describes a process for detecting prion protein in a sample by mixing the sample with a non-pathogenic protein and a chelating compound and subjecting the mixture to ultrasound to amplify the prion protein.

EP2280028 A1 describes the amplification of prion protein derived from sheep scrapie by repeatedly sonicating in the presence of normal prion protein, e.g. of rodent origin.

US2009/0047696 describes that amplification of proteinase K resistant prion protein from a mixture of normal prion protein with seeding protein is influenced by the presence of tenside, namely SDS or Sarkosyl.

OBJECTS OF THE INVENTION

It is an object of the invention to provide an alternative device and method for producing aggregated conformation prion protein from native conformation prion protein, wherein the aggregated conformation prion protein preferably is of one uniform conformation.

GENERAL DESCRIPTION OF THE INVENTION

The invention achieves the above-mentioned objects by providing a device and a method for producing prion protein having an aggregated conformation as defined in the claims, and especially by a device and method using the device, in which method native conformation prion protein is contacted with aggregated conformation prion protein in a liquid preparation and subjected to at least one cycle or to a number of cycles of application of shear-force for fragmenting aggregates of prion protein, wherein the shear-force applied is precisely controlled, e.g. to a range of 10%, preferably 2%, more preferably to 1%, more preferably to 0.5% intensity range around one shear-force intensity value, wherein optionally each cycle contains at least one second phase of incubation without agitation and/or at least one phase of agitation at one shear-force intensity value, which is different from the first shear-force intensity value, which is e.g. zero or 1 to 50%, preferably zero of the first shear-force intensity value. The second phase of incubation, also referred to as a resting phase, is included for allowing the aggregation of native conformation prion protein with aggregated conformation prion protein. In addition to this process for amplification of aggregated state prion protein from native conformation prion protein, the invention relates to the aggregated state prion protein obtained by the amplification process, which aggregated state prion protein has one conformation, which is e.g. identical within one batch and reproducible between batches, e.g. as detectable by proteinase resistance in a Western blot and/or by structure sensitive spectroscopy, e.g. by NMR, especially $^{13}$C-NMR, or fluorescence spectroscopy. Optionally, the product of the process of the invention can be used as aggregated conformation protein which in admixture with native conformation prion protein is subjected to at least one cycle or to a number of cycles of application of shear-force for fragmenting aggregates of prion protein as described herein.

Native conformation prion protein can e.g. be produced by expression in a cultivated cell which is genetically manipulated to contain an expression cassette encoding the prion protein and isolating the prion protein from the cultivated cell and/or from the medium of a culture of the cells. Cells for expression of prion protein can be bacteria, preferably *E. coli*, yeast, fungi, and mammalian cells, e.g. human cells or hamster CHO cells. Native conformation prion protein can also be produced from mammalian tissue.

During the preparation of this invention, it has been found that the amplification of aggregated conformation prion protein from a liquid preparation containing native conformation prion protein and prion protein in the aggregated conformation using agitation by ultrasound or by shaking is volume-dependent and yields of protease-resistant prion protein are hardly reproducible.

Detailed analysis has shown that the amplification of aggregated conformation prion protein using agitation by ultrasound is dependent on the position of the reaction vessel containing the liquid preparation with respect to the sonotrode surface, and is also dependent on the spacing of the reaction vessel from the sonotrode surface.

In contrast, when subjecting according to the invention a liquid preparation of native conformation prion protein in contact with prion protein having the conformation of its aggregated state, to a shear-force that is controlled by limitation to one intensity with a variation or range of at maximum of 10%, preferably of 5%, more preferably of 1%, more preferably to 0.5% of the intensity, which shear-force is applied to each volume element of the liquid preparation, a reproducible generation of prion protein having the conformation of an aggregated state, preferably having the conformation of one specific aggregated state, is obtained at reproducible yield. Preferably, the shear-force transmitted to the liquid preparation consists of the controlled intensity shear-force in order to apply shear-force of a limited range of intensity only to the liquid preparation. More preferably, this controlled intensity shear-force is of the maximum intensity transmitted to each volume element of the liquid preparation. When using the generation of the shear-force by ultrasound, the control to the limited intensity range is preferably obtained by positioning the entire volume of the liquid preparation at equal distance between pre-determined vibration nodes of the sonicator (also referred to as a sonotrode) and at the distance from the sonicator where maximum amplitude is generated for one frequency, preferably for the resonant frequency of the sonicator. Further, it has been observed that the conformation of the prion protein in its aggregated state conformation can differ form its native state in dependence on the shear-force intensity, as e.g. detected by the resistance to Proteinase K digestion, followed by PAGE (separation of protein by polyacrylamide gel electrophoresis), preferably as detected by Western blotting using an antibody specific for the prion protein to identify prion protein that is immobilized following PAGE, e.g. differing aggregated state conformations of prion protein can be detected for differing shear-forces applied to native conformation prion protein.

Generally, for the purposes of the invention, the native conformation of a prion protein relates to the wild-type conformation of the protein, as e.g. observed in healthy mammals, which native conformation is generally soluble in physiologic aqueous solution. In contrast, the misfolded conformation, which is associated with amyloid-like aggregates forming disease in mammals, which is generally insoluble in physiologic aqueous solution, and is e.g. at least partially resistant to proteolytic degradation by enzymes, e.g. by Proteinase K, is also referred to as the conformation of the aggregated state, the aggregated conformation and/or as the disease-associated conformation, which conformation is e.g. transmissible to the native conformation, and is therefore also considered to represent a disease-transmitting or infectious conformation, e.g. for the natural disease-associated aggregated conformation.

In accordance with the peculiarities of amyloid-like aggregate associated diseases, which involved the formation of the disease-associated aggregated conformation of prion protein, which disease-associated conformation can be formed from the wild-type native conformation, the in vitro generation of prion protein in its disease-associated aggregated conformation by incubation of native conformation prior protein with prion protein in its aggregated conformation is also referred to as amplification, referring to the amplification of the disease-associated aggregated state in originally native conformation prion protein. Further, for the purposes of the invention, the conformation of the aggregated state in addition to aggregated conformations observable in mammals also includes an aggregated conformation which is generated in vitro, and which may not be observable in a mammal suffering from an amyloid-like aggregate associated disease. The reason for optionally including non-natural aggregated conformations of prion protein is that it has been observed during the preparation of the invention that more than one aggregated state of one homogenous peptide, i.e. a peptide having one identical amino acid sequence, can be generated by an in vitro amplification, induced by contact with one preparation of prion protein in its aggregated state, e.g. as originally derived from tissue of a mammal suffering from an amyloid-like aggregate forming disease.

Generally, the state of the conformation of an individual peptide refers to each individual peptide, i.e. irrespective from the aggregation or presence as individual, non-associated peptides of prion protein, e.g. in its native conformation and/or in its aggregated conformation.

It has been found that the application of a large intensity range of shear force to aggregates that include aggregated conformation prion protein can result in the generation of different conformation species of prion protein having the same amino acid sequence, which different conformation species e.g. are characterized by having a different resistance against proteolytic degradation, e.g. against Proteinase K digestion. For example, fragmentation by shear-forces generated by a rotating element arranged within a coaxial pipe at rotation speeds between 20 and 1300 Hz (rotations per second) gave at least two fractions of aggregated conformation prion protein that differed in their resistance against Proteinase K, whereas application of a narrow range shear-force intensity, e.g. limited to a maximum range of 10% or less of the maximum shear-force, resulted in reproducible production of aggregated conformation prion protein of one and the same conformation from native conformation prion protein, e.g. with shear force intensity controlled to a range of 10%, preferably 2%, more preferably 1%, most preferably 0.5 to 0.1%. On the example of hamster prion protein, it was found that the amplification is dependent on the shear-force intensity, as shear-forces by different rotation speeds resulted in an effective generation of aggregated conformation prion protein at distinct intensity ranges, e.g. at three different rotation speeds, significantly increased amplification was found. This result shows that amplification is dependent on the shear-force intensity and that specific aggregated conformation prion protein is generated at different shear-forces. This indicates that the controlled shear-force intensity used for amplification of aggregated conformation prion protein results in different and homogenous species of aggregated conformation prion protein because these aggregated conformations are specific for the shear-force intensities. The homogeneity of aggregated conformation prion protein produced according to the invention, e.g. in comparison to prion protein subjected to a wide range of shear-force, i.e. from uncontrolled amplification could also be shown in structure-sensitive spectroscopy, e.g. in NMR.

In addition, it was found that the application of a narrow range shear force intensity resulted in reproducible high conversion rates from native conformation prion protein to aggregated conformation prion protein, which can also be referred to as a high yield that is reproducible.

In a first embodiment, the invention provides a device for use in generating aggregated conformation prion protein from a liquid composition of native conformation prion protein with aggregated conformation prion protein, the device comprising a shear-force generator which is controlled to induce shear force consisting of one intensity with an intensity range of maximally 10%, preferably 2%, more preferably 1%, most preferably 0.5 to 0.1%, to each volume element of the liquid preparation, and preferably the device comprises at least two walls confining the space in which the shear-force of one intensity occurs, which space is in flow connection to or containing the total liquid composition volume.

In a second embodiment, the invention provides a process for producing aggregated conformation prion protein from a liquid composition comprising native conformation prion protein and aggregated conformation prion protein which is an initial or starter aggregated conformation prion protein, the process using the controlled shear-force. Optionally, the process can include the detection of the amount and/or conformation characteristics, e.g. by protease digestion and/or size separation and/or immunological detection and/or structure sensitive spectroscopy methods, e.g. NMR and/or fluorescence spectroscopy, as an analytical process. In this embodiment, an analytical process is also provided for detecting the presence of aggregated conformation prion protein within a sample, as the sample is the aggregated conformation prion protein and the application of controlled shear-force in the presence of native conformation prion protein generates aggregated conformation prion protein from the native conformation prion protein in dependence on the presence of aggregated conformation prion protein in the sample. Accordingly, in this analytical process, the detection of the generation of aggregated conformation prion protein from the native conformation prion protein indicates the presence of aggregated conformation prion protein in the original sample.

In addition, the process may include the addition of a compound, prior to, during and/or following application of the controlled shear-force, e.g. for detecting an influence of the compound on the behaviour of the native conformation prion protein in the process, i.e. under the controlled shear-force.

Generally, the device contains a control unit which is set for controlling the shear-force generator to at least one pre-set shear force intensity to a range limited to a maximum of 10% of one shear-force value, e.g. of the maximum shear-force, e.g. by setting or controlling a drive contained in or coupled to the shear-force generator to a maximum range of 10% of one frequency, e.g. to a maximum of 10%, preferably of 1% or 0.1% of one frequency, e.g. of a pre-determined frequency or of the resonance frequency of the shear-force generator.

In one embodiment, the shear-force generator can comprise or consist of a rotary element arranged in a sample vessel having a lid, wherein the rotary element is run on bearings which are coaxially arranged within the sample vessel, and wherein the rotary element comprises a first coupling element of a coupling, e.g. a permanent magnet, which preferably is at least bipolar or quadrupolar. The first coupling element is arrangeable for coupling with the second coupling element of the coupling, e.g. a driving coil arrangement which can be arranged surrounding the first coupling element. Preferably, the outer surface of the rotary element is parallel to the inner wall surface of the vessel, e.g. the rotary element and a coaxial section of the inner wall surface of the vessel are spaced and cylindrical or conical. Preferably, the bearing of the rotary element comprises or consists of an axle, one end of which is arranged contacting a bottom section of the inner vessel surface and the other end of which runs in a bearing attached next to the rim of the vessel, e.g. by frictional connection and/or by positive fit.

Alternatively, the shear-force generator can have a rotary element coaxially arranged in a radially spaced tube section, the radial spacing of the rotary element and the tube and the axial section in which both the rotary element and the tube extend defining a space, e.g. of ring-shaped cross-section, in which space upon rotation of the rotary element shear force is generated. Preferably, the rotary element along its longitudinal and rotary axis has a constant outer diameter and is arranged at a constant spacing from the encircling tube section. The rotary element can take any outer form, preferably of axial symmetry, e.g. a flat shape or a rectangular cross-section and preferably has a cylindrical outer surface. Preferably, the tube in its section encircling the rotary element has a cylindrical inner cross-section. Along the common longitudinal axis, the tube preferably at one end of the section encircling the rotary element extends over the rotary element, such that the rotary element ends at a distance from the end of the tube, allowing a suction action at rotation of the rotary element, and at the opposite end of the section encircling the rotary element, the rotary element extends over at least one exit opening in the walls of the tube, allowing liquid to exit. Preferably, the at least one exit opening in the walls of the tube has a cross-section of at least the cross-section of the area between the tube and the rotary element, more preferably, the exit opening has a cross-section of or greater than the inner cross-section of the tube, and most preferably, the exit opening is the cross-section of the tube.

This shear-force generator is arranged within a vessel containing a liquid preparation of prion protein, as rotation of the rotary element in addition to exerting a shear force of one pre-set intensity, which is controlled to a narrow range, generates a suction at the end which is protruded by the encircling tube section such that all volume elements of the liquid are moved through the space between the rotary element and the encircling tube section, where the volume elements are consecutively subjected to the shear force.

The rotary element is arranged in a bearing, which is preferably coaxial to the tube and to the rotary element, e.g. the bearing can be arranged in a tube section adjacent the at least one exit opening and opposite the section encircling the rotary element. Preferably, the bearing comprises or consists of a low-friction polymer tube, e.g. poly tetrafluoro ethylene (PTFE), optionally having at least 2 or at least 4 longitudinal convex or concave folds, arranged in a tube section adjacent the exit openings, between the rotary element and the tube encircling it. The low-friction polymer tube of the bearing preferably is arranged between one circumferential shoulder extending from the rotary element and one circumferential shoulder protruding from the inner surface of the tube, e.g. one shoulder at one of the opposite ends of the bearing.

Preferably, the shear force generator is controlled to one pre-set shear force corresponding to a rotation rate between 10 and 10.000 Hz, preferably between 50 and 5000 or up to 2000 or 1000 Hz, precisely controlled to a range of maximally 1% of the rotation rate set, more preferably to a rotation rate with range of maximally +/-2 Hz, more preferably of maximally +/-1 Hz, with an outer diameter of the rotary element of 1.95-2.05 mm arranged in a tube section with an inner diameter of 1.55-2.75 mm, wherein the rotary element is a cylinder, optionally having a square flat end section.

In the alternative, the shear force generator can be a sonicator, also referred to as an ultrasound emitter, which has a vessel for receiving the liquid preparation having an inner volume which extends for a volume element only that is arranged in the distance from the sonicator surface (or sonotrode surface) and is parallel to the surface section only, in which at least 75% to 90%, preferably at least 95%, more preferably at least 99% of the maximum amplitude is positioned. This volume element is e.g. arranged within the distance of 0.5 mm to 50 mm from the surface of the sonicator and extends parallel to the center of the surface fraction between vibration nodes of the sonicator surface, e.g. for maximally 10%, preferably for maximally 2% or 1% of the area between vibration nodes. The position of the volume element can e.g. be pre-determined by calculation of the surface fraction of the sonotrode surface and the distance from the sonotrode surface in which maximum amplitude, and hence maximum shear-force is generated. Due to the specific arrangement of the volume element in the maximum vibration intensity, the liquid composition therein is subjected to a shear force having an intensity of a limited intensity range. For an efficient transfer of vibrations from the sonotrode surface to the volume element, the vessel preferably consists of a material that is permissive to ultrasound, e.g. of polypropylene, poly tetrafluoro ethylene (PTFE) or other types of teflon, and a transfer liquid, e.g. water, is arranged between the vessel and the sonotrode surface. Preferably, the sonotrode forms one wall of a transfer liquid bath, e.g. a side wall and preferably the bottom wall, and the height of the transfer liquid in perpendicular to the sonotrode surface is set to one wave-length of the ultrasound, e.g. at the resonance frequency of the sonotrode, or to an integral multiple of the wave-length of the ultrasound, e.g. at the resonance frequency of the sonotrode. The transfer liquid bath can be adapted or designed to pre-set the height of the transfer liquid, the height being determined in perpendicular to the sonotrode surface.

Preferably, the devices are arranged in an array of, two or more devices, preferably 7, 14 or 21 devices, arranged with their longitudinal axes vertically in a temperature controlled housing. All devices of the array can be connected to and controlled by one computer, which is provided for controlling the rotation rate of each rotary element individually. This array of devices is advantageous for treating aliquots of one liquid composition of prion protein in parallel, i.e. without variation of the composition or state of the liquid composition, as e.g. could occur in subsequent treatment processes during storage of aliquots and day-to-day variations of treatment conditions. Using the array of devices, the process of the invention comprises the treatment of aliquots of one liquid composition of prion protein in separate single devices concurrently, preferably with differing shear forces each, which are generated by different rates of rotation applied to the rotary elements.

Accordingly, a process using the device comprises the step of apportioning aliquots of a liquid preparation to a number of identical vessels, which aliquots preferably are fractions taken from one homogenous liquid composition. Optionally, aliquots can be subjected to the same or each to a different shear force intensity. Further optionally, samples, e.g. mammalian samples can be used as the aggregated conformation prion protein, and/or compounds suspected of affecting the amplification or aggregation process can be added to aliquots for comparing the change in conformation from native conformation prion protein to its aggregated conformation between aliquots, e.g. comparing quantity of amplification and/or quality of amplification, e.g. by quantitative and/or qualitative analysis of the obtained aggregated conformation, preferably in Western blots of proteinase-treated aliquots of the processed samples.

In a particular embodiment, the vessel is a tube connected with a pump, which tube only crosses the volume element that is arranged in the distance from the sonicator surface and is parallel to the surface section only, in which at least 75% to 90%, preferably at least 95%, more preferably at least 99% of the maximum amplitude is positioned. This volume element is e.g. arranged within the distance of 0.5 mm to 50 mm from the surface of the sonicator and extends parallel to the center of the surface fraction between vibration nodes of the sonicator surface, e.g. for maximally 10%, preferably for maximally 2% or 1% of the area between vibration nodes.

In a preferred embodiment, the device comprises a controlled positioning apparatus that is disposed to position a reaction vessel holding the liquid composition containing prion protein. The positioning apparatus can be mechanically controlled and/or computer-controlled to position the reaction vessel in relation to the shear-force generator. For example, the positioning apparatus can have a clamping means for releasably fixing the reaction vessel, preferably in a pre-determined position, e.g. adjacent an abutment face arranged within the clamping means. The clamping means can be arranged on a holder of the positioning apparatus, the holder being movable, e.g. mounted on a computer-controlled mechanical arm. In the alternative or additionally, the holder can be guided for positioning, e.g. by the holder being engaged in a thread of an element, e.g. a lid, arranged at a fixed distance to the sonotrode surface. In this embodiment, the reaction vessel preferably can be sealed prior to arrangement in the clamping means.

The controlled positioning apparatus allows the process to comprise the step of positioning the reaction vessel at varying positions to the shear-force generator, e.g. in a process for determining the position of the reaction vessel in which its inner volume receives the maximum amplitude of sonication.

In another alternative or additional embodiment, the controlled positioning apparatus is adapted to repeatedly position a reaction vessel adjacent the shear-force generator during application of the shear-force and to remove the reaction vessel from the shear-force generator during a resting phase, e.g. by depositing the reaction vessel at a distance from the shear-force generator. Herein, a rotary element within a tube can be mounted within the reaction vessel with a first coupling element to the rotary element being accessible by an external drive, e.g. by direct contact or without direct contact to the drive, e.g. a permanent magnet. The positioning of the reaction vessel by the positioning apparatus also in this embodiment positions the reaction vessel functionally adjacent the shear-force generator by providing the coupling of the first coupling element to the second coupling element, e.g. mounted to a drive, e.g. a driving coil arrangement. This embodiment allows a more effective use of the shear-force generator and of a drive, respectively by the controlled positioning apparatus being adapted to subsequently position at least two reaction vessels adjacent the shear-force generator during the application of shear-force, because the controlled positioning apparatus is adapted to remove the reaction vessels from the shear-force generator during the resting phase. This allows the subsequent application of shear-force to at least two reaction vessels, e.g. a process for parallel application of controlled shear-force to at least two reaction vessels using one shear-force generator.

For producing aggregated conformation prion protein using the device, a liquid composition containing native conformation prion protein and one or a mixture of aggregated conformation prion protein is positioned or moved through the volume element, in which shear force consisting of one intensity with an intensity range of maximally 10%, preferably 2%, more preferably 1%, most preferably 0.5 to 0.1% is generated, as a fragmentation phase, e.g. for is to 240 s, preferably for 30 to 120 s, preferably with a subsequent resting phase, e.g. for 10 s to 1080 s, preferably 60 s to 540 s. More preferably, the fragmentation phase and the subsequent resting phase are performed in cycles, e.g. 5 to 500 cycles, preferably 60 to 280 cycles, more preferably 100 to 140 cycles.

In one embodiment, the process for generating aggregated conformation prion protein from aggregated conformation prion protein is an analytical process, wherein a sample, e.g. body fluid from a mammal, preferably spinal cord liquor or blood serum, is added to native conformation prion protein to form a liquid composition containing the sample and the native conformation prion protein, which liquid composition is subjected to the controlled pre-set shear-force of a limited intensity range of the invention, and detecting an increase of aggregated conformation prion protein, e.g. of protease resistant prion protein, preferably in PAGE and/or in a Western blot. In this embodiment, the advantage of the process, namely to reproducibly generate aggregated conformation prion protein at high yield, due to the precise control of the shear force intensity applied, is used to determine that the original sample contained aggregated conformation prion protein when an increase of the aggregated conformation prion protein is detected.

Optionally, the aggregated conformation prion protein generated by the process of the invention can be used as a positive control sample in analytical processes that contain the step of amplifying the aggregated conformation prion protein from an excess of native conformation prion protein, as the aggregated conformation prion protein produced by the process of the invention has a uniform aggregated conformation which under the controlled shear force is reproducibly amplified. The uniform aggregated conformation of the prion protein produced is at least as uniform as determined by or for use in characterization by protease digestion, e.g. in a method of detecting aggregated conformation prion protein by protease digestion and detection of protease resistant digestion products.

Accordingly, the analytical process preferably comprises subjecting one positive sample in parallel to the samples obtained from a mammal to the process steps, which positive sample contains the aggregated conformation prion protein generated by the process of the invention.

In a further embodiment, the process for production of aggregated conformation prion protein includes the step of contacting the aggregated conformation prion protein with a probe compound and the step of determining the occurrence of an interaction of the probe compound with aggregated conformation prion protein. Preferably, the step of determining the occurrence of the interaction comprises the determination of an inhibitory effect of the probe compound onto the amplification of the aggregated conformation prion protein.

DETAILED DESCRIPTION OF THE INVENTION

Figure 2:
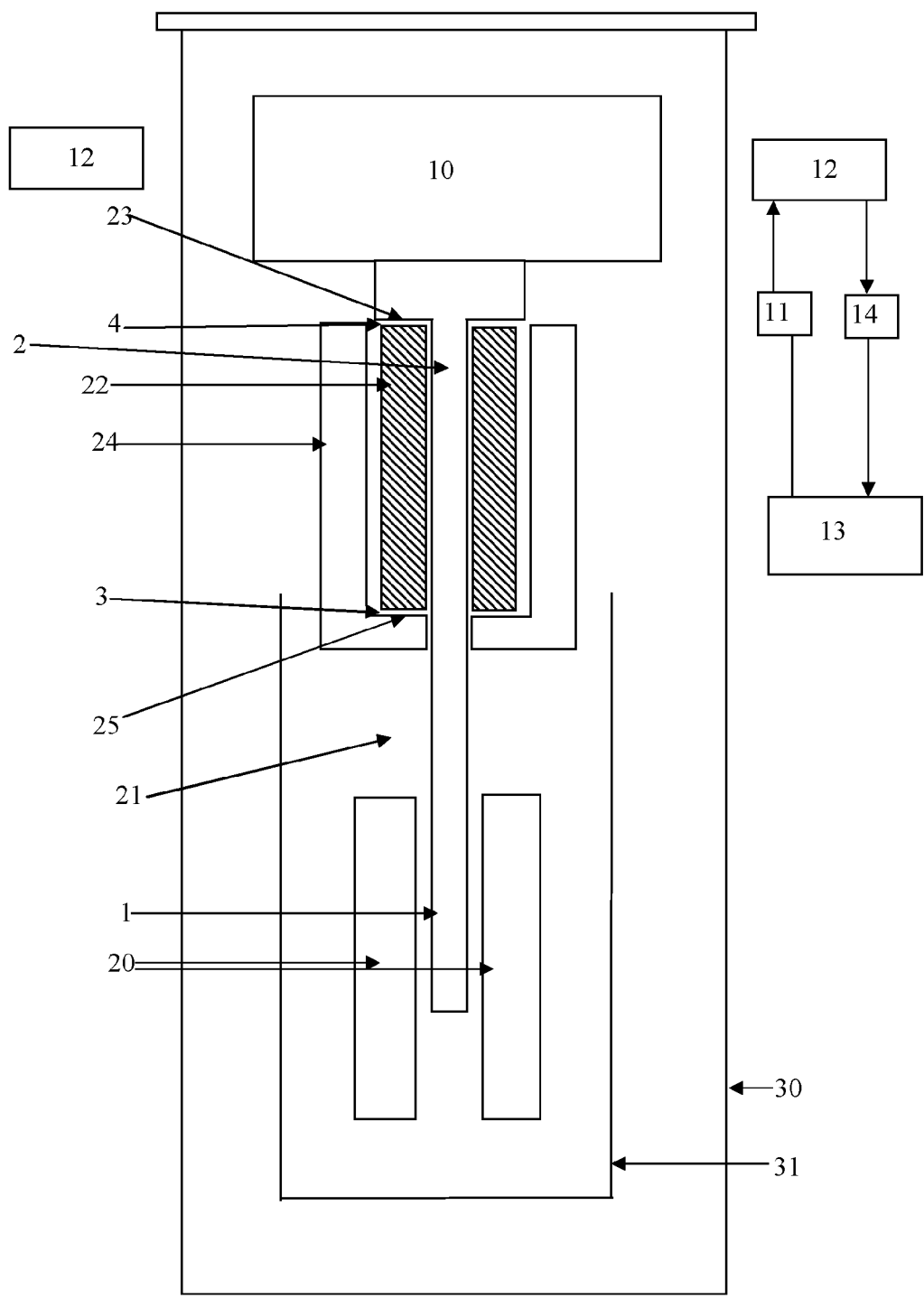
Figure 3A:
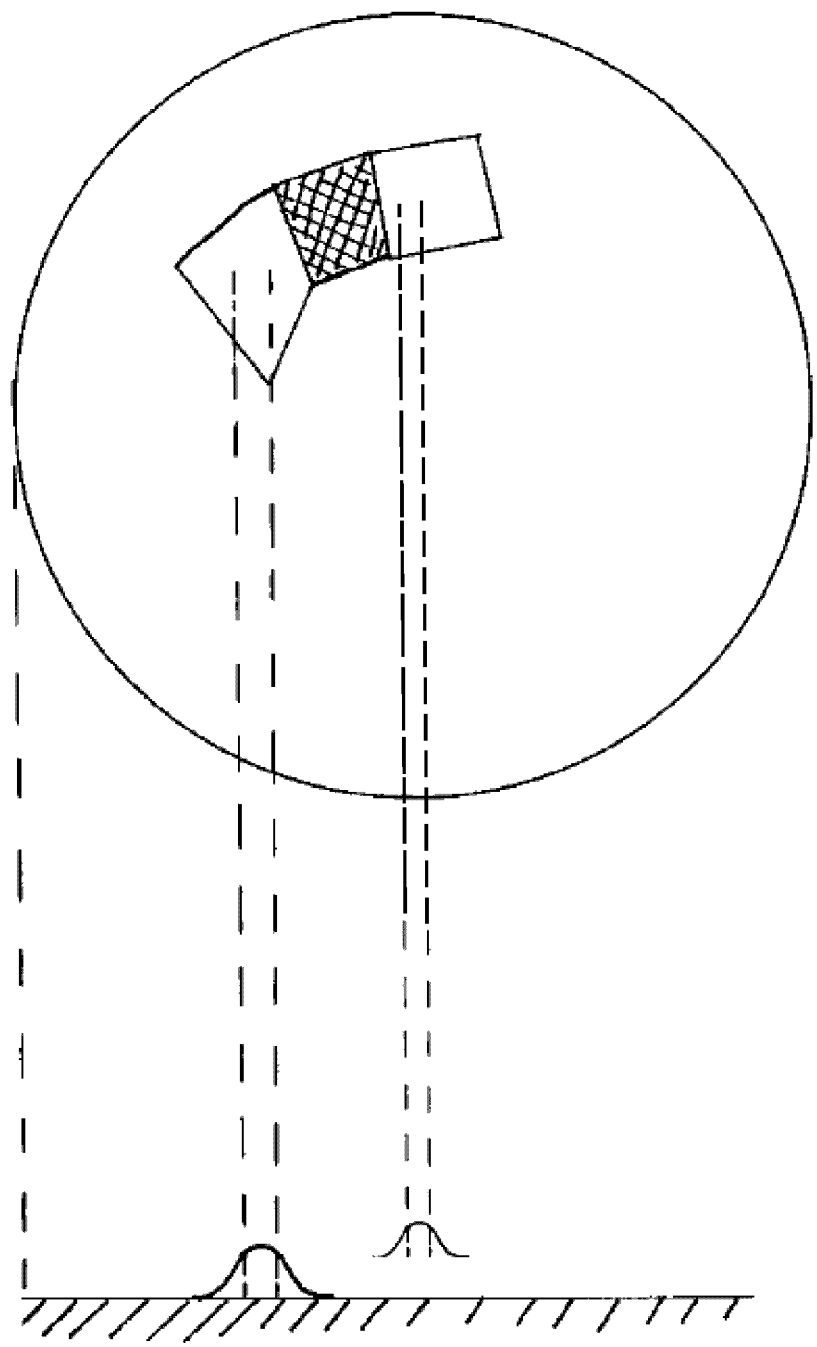
Figure 3B:
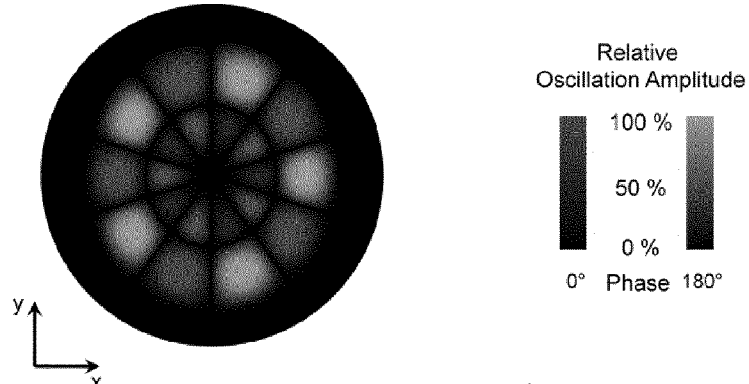
Figures 3C, 3D:
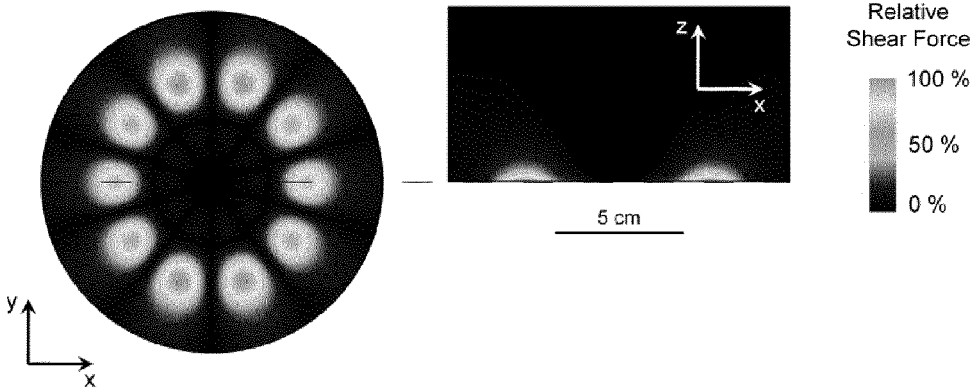
Figure 4:
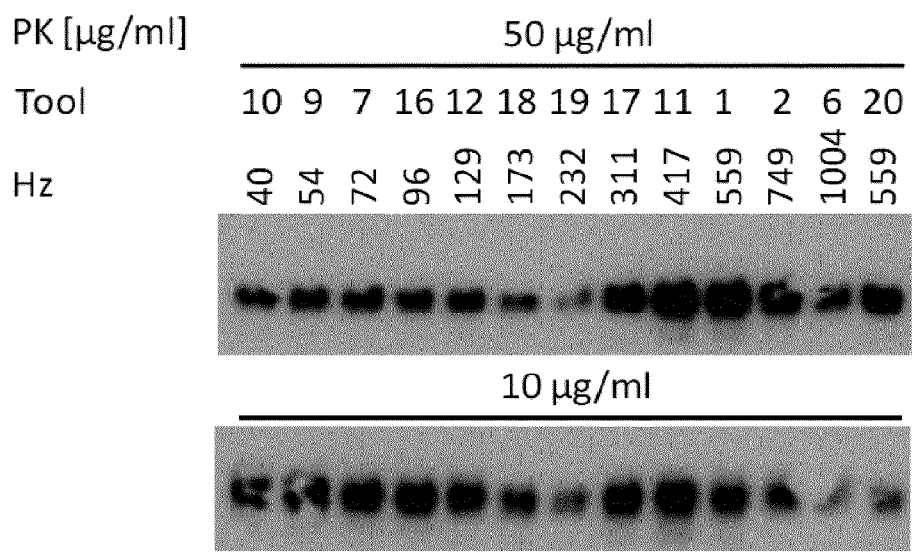
Figure 5:
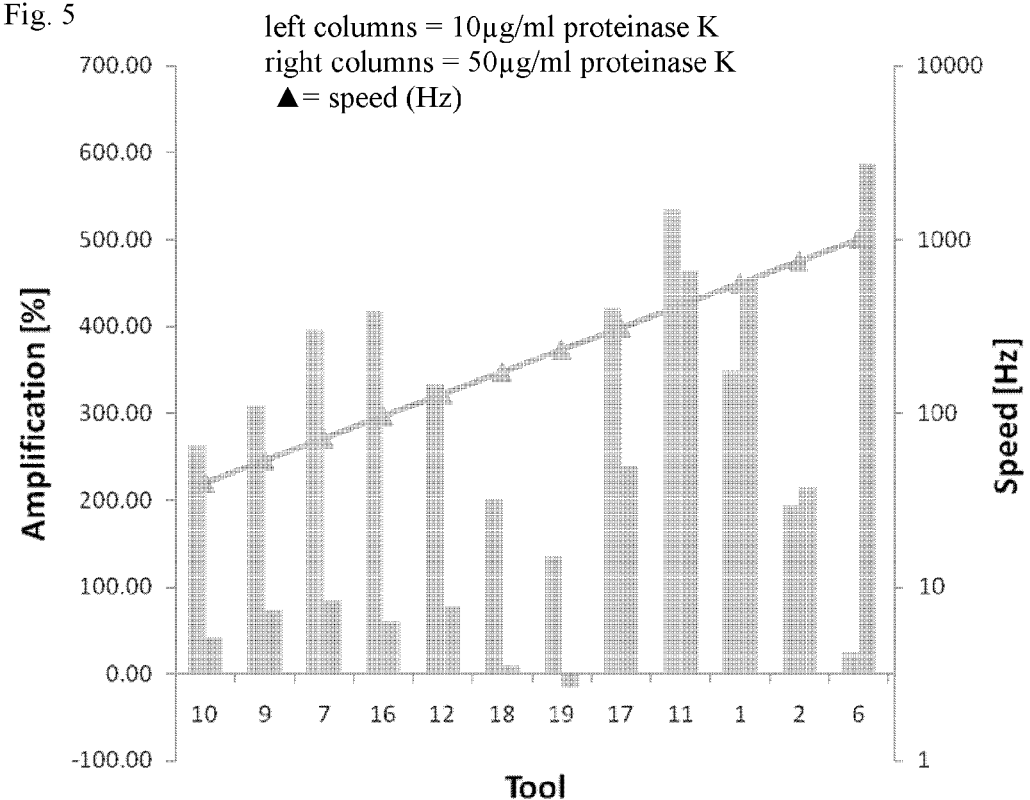

The invention is now described in greater detail with reference to the figures, wherein FIG. 1 schematically shows a shear force generator of the invention, FIG. 2 schematically shows another shear force generator of the invention, FIG. 3A schematically shows a sonotrode as a shear-force generator, with the areas between vibration nodes (hatched) and shear-force intensities (white boxes) represented in the lower side view, FIG. 3B shows a top-view onto a sonotrode as a shear-force generator of the invention with vibration amplitudes given in grey shading according to the right-hand scales, FIG. 3C shows a top-view onto a sonotrode with vibration amplitudes at a distance of 0.5 mm above the sonotrode surface, FIG. 3D shows the shear-force intensity at a distance of 0.5 mm above the sonotrode surface in a partial cross-section of FIG. 3B as indicated by the dashed line in grey shading according to the right-hand scale, FIG. 4 shows Western blots of Proteinase K digested aggregated conformation prion protein produced according to the invention with different shear forces applied, FIG. 5 shows a graph of the normalized concentrations of aggregated conformation prion from the Western blots of FIG. 4, FIG. 6 shows a Western blot analysis of Proteinase K digested aggregated conformation prion protein produced according to the invention with different shear forces applied, FIG. 7 shows sections of Western Blots of proteinase K-resistant prion protein produced at different controlled shear-forces, FIG. 8 shows a graphic analysis of the relative amount of aggregated conformation prion protein of FIG. 7, FIG. 9 shows the kinetics of the amplification at controlled shear-forces (Hz), FIG. 10 shows shows an SDS-PAGE (silver stained) of the initial admixture of Sc237 with the native conformation prion protein (left lane) and of the produced aggregated conformation product, FIG. 11 shows the CP-MAS NMR: $^{13}C$, $^{13}C$ correlation of a comparative spontaneous amplification product, FIG. 12 shows the CP-MAS NMR: $^{13}C$, $^{13}C$ correlation of an amplification product produced according to the invention, FIG. 13 schematically shows an embodiment of a shear-force generator in cross-sectional view, and FIG. 14 shows an embodiment of a holder for holding a reaction vessel.

In the examples, same reference numerals refer to functionally identical elements.

FIG. 1 depicts a device containing a rotary element 1, which is arranged on an axle 2 that is coaxial to the vessel and runs on a first bearing 3 and a second bearing 4. The first bearing 3 is formed by a first end of axle 2 contacting the bottom of vessel 5, in which the rotary element 1 is arranged, and the second bearing 4 is formed by the second end of the axle 2 opposite its first end. As preferred, the second bearing is formed by a boring 6 of a holder 7, which is e.g. held by frictional connection within a recess formed within the lid 8. The rotary element 1 comprises a first coupling element 10 of a coupling, e.g. a permanent magnet having at least two poles, which coupling is connected to a drive 11. For driving the rotary element 1, the device is arranged in a coupling position to the second coupling element 12, e.g. between coils, and the drive 11 is an electric field generator connected to the coils. The drive 11 is closely controlled by a control unit 13, which preferably is also connected to a sensor 14 monitoring the drive 11. The control unit 13 is equipped to control the drive 11, e.g. in a closed loop circuit, to high precision for generating a shear force having an intensity range of 2%, preferably of 1% or narrower about one intensity value, e.g. by controlling the rotation of the rotary element 1 within vessel 5 to one frequency with a variation of 2%, preferably 1% maximally.

The surface of the rotary element 1 can be parallel to the wall of the vessel 5, forming a homogenous shear force for a cylindrical rotary element in a cylindrical vessel 5. In the case of a conical vessel 5, a rotary element that is conical for being in parallel to the vessel 5 will generate a shear force gradient in accordance with the change in radius. Generally, if the shear force gradient caused by the angle of the conical shape of the vessel and the parallel conical shape of the rotary element exceeds the narrow range of one shear force intensity, it is preferred that the angle of the cone of the rotary element is smaller to the axle than the cone of the inner vessel wall to its longitudinal axis, preferably such that the spacing between the vessel and the rotary element increases with increasing radius of the rotary element and vessel, respectively.

This embodiment has the advantage that it can be realized using a commercial vessel 5, e.g. an Eppendorf vial, into which the rotary element 1 is positioned and held by a second bearing 4 which is provided by a plate serving as a holder 7 arranged in a recess of a lid 8.

Rotation of the rotary element 1 within vessel 5 at a closely controlled rotation frequency, i.e. at a narrow range about one pre-set rotation frequency generates a shear force of a narrow range about one pre-set shear force between the rotary element 1 and the vessel 5.

FIG. 2 shows a preferred embodiment of the device of the invention, wherein a rotary element 1 is encircled by a spaced tube 20 of cylindrical inner diameter, the inner wall of the tube 20 forming a space of annular cross-section around the rotary element 1. In the alternative, a section of the rotary element 1 that is encircled by tube 20 can have a flat form, e.g. of rectangular cross-section not exceeding, preferably having the radius of the rotary element 1. As preferred, the tube 20 exceeds the first (lower) end 1*a* of the rotary element 1, and the tube 20 provides for an exit opening 21 having or exceeding the diameter of the cross-section between the rotary element 1 and tube 20. The rotary element 1 runs on a first bearing 3 which is formed by a low-friction polymer tube 22 arranged between the axle 2 of the rotary element 1 and a sleeve 24 that arranged around axle 2, wherein the sleeve 24 has an inner shoulder 25 against which the low-friction polymer tube 22 abuts, and a second bearing 4 which is formed by shoulder 23 and the low-friction polymer tube 22 abutting against the shoulder. The sleeve 24 and the tube 20 are coaxial and can optionally be formed of one tube having the exit opening 21, e.g. at least one boring and preferably 2 opposite borings, arranged between the sleeve 24 and the tube 20. Preferably, the sleeve 24 and the tube 20 are connected to one another, e.g. by at least one connector, preferably by at least 1, preferably two sections of a tube, which sections separate the exit openings 21.

A first element of a coupling 10, e.g. a permanent magnet, is fixed to the axle 2. Preferably, the device is encased within a sealable housing 30, and the second element of the coupling 12 is arranged outside the housing 30, allowing the drive 11 coupled to the second element of the coupling 12 to drive the first element of a coupling 10, and hence the axle 2 which bears the rotary element 1.

The embodiment of the device depicted in FIG. 2 is for arrangement of the tube 20 within a vessel, which can e.g. be the housing 30, or which vessel 31 can be arranged with in a housing 30. This embodiment has the advantage that the shear force is generated without interaction with the vessel 31.

FIG. 3A shows a sonotrode surface in top view, wherein the hatched dark area indicates one of several vibration nodes, and adjacent surface areas which significantly vibrate. The lower side view shows that the one exemplified vibrating area generates shear-force which is limited both to a surface section of the sonotrode and to a certain spacing from the sonotrode surface, as indicated by the curve that represents both the spatial extent of the vibration, i.e. shear-force maximum in parallel to the plane of the sonotrode surface, and in the distance form the sonotrode surface.

FIG. 3B shows a sonotrode surface in top view, wherein the dark area schematically shows one of several node forming areas and adjacent surface areas which significantly vibrate. The dark lines represent vibration nodes, and increasing brightness shows increasing shear-force. FIG. 3C shows the spatial distribution of shear-force at a hight of 0.5 mm above the sonotrode metal surface as determined e.g. in water. The side view given in FIG. 3D shows that the vibrating areas are not only limited to a surface section of the sonotrode, but are also limited to a certain spacing from the sonotrode surface, as indicated by the intensity curve of the shear-force between vibration nodes, which curve represents both the spatial extent of the vibration energy maximum in the plane of the sonotrode and the distance from the sonotrode surface, to which the vibration energy maximum extends. The shear force of one intensity that is used in the invention is exerted only onto the volume elements of a liquid composition which are located in the volume above the sonotrode in which maximum vibration energy is generated. Accordingly, in devices and processes using a sonotrode as the shear force generator, all the volume elements of the liquid composition are arranged in a distance from the sonotrode surface and in parallel to a surface fraction of the sonotrode surface between vibration nodes, in which the vibration energy maximum is generated, preferably at a resonant frequency of the sonotrode, e.g. allowing a specific maximal ultrasonic shear force of a limited intensity range only to be transmitted to the vessel's inner volume consisting of the volume elements of the liquid composition, e.g. to a precision or limitation of 10%, preferably 2% or 1% of the shear-force maximum at the one frequency applied. It has been found that additional agitation for mixing the liquid preparation is not necessary, as the shear-force applied to each volume element of the liquid composition consists of the controlled intensity range of shear-force, which results in the homogeneity of aggregated-state prion protein generated from the native conformation prion protein in admixture with aggregated state prion protein of the liquid composition.

Example 1

Device for Generating Controlled Shear-Force of a Limited Intensity Range

As an example, a device as schematically shown in FIG. 2 was used with the following dimensions: a rotary element with a square cross-section of 1.95 mm on an axle of 1.95 mm diameter was arranged at a spacing of 0.3 mm coaxially in a cylindrical tube. The sleeve, the tube and the rotary element including the axle arranged in the sleeve and the permanent magnet at the end of the axle opposite the square rotary element were obtained from Heidolph, Germany, and the original exit borings were drilled to diameter of 3 mm to form two opposing exit borings of 3 mm diameter each arranged adjacent the tube.

The bearing was as shown in FIG. 2, using a Teflon tube cut to size between the shoulder of the axle and the inner shoulder of the sleeve. For reduced friction, the Teflon tube was folded lengthwise by flattening two times, generating 4 lengthwise folds separating 4 lengthwise convex sections, as is generally preferred for this tube. The sleeve was formed by a tube section that was connected to the tube encircling the rotary element by the tube wall sections forming the boundaries to the exit openings. For the coupling, the set of stator coils available from Heidolph were used, including part of their individual control electronics.

For forming an array of the devices, two or more devices, preferably 14 or 21 were arranged with their longitudinal axes vertically in a temperature-controlled housing. All devices of the array were controlled by one computer.

The shear rate was controlled by a potentiometer and multimeter, regulating the rates of rotation between 20 to 1300 Hz with a variation of 5 Hz, preferably 2 Hz, and more preferably of 1 Hz.

It was found that these devices could be run for 136 cycles of 60 s rotation at 20 to 1300 Hz and 540 s resting phase without rotation with an accuracy of rotation of 1 Hz for treatment of aqueous liquid compositions at 5° C. to 40° C. in one experiment, and these devices could be used for up to 10 experiments. The bearing was essentially stable, maintained a low-resistance movement of the rotary element which is essential for reproducibility of rotation rates, and did not show excessive wear.

As a comparative bearing, a rolled-up sheet of PTFE foil was arranged between the rotary element and the tube. After rotating for 10 cycles of 60 s with 540 s resting phase, the rolled-up sheet forming the bearing had run hot and was partially destroyed, whereas a bearing consisting of a PTFE tube arranged between the rotary element and a tube section could run for at least 5 min at the same speed, and could be used to a total service life of at least 60 min up to 24 h.

For comparison to a device of the invention having two exit openings with a total cross-section of the cross-section that is limited by the rotary element and the tube section encircling it, a device was used, wherein the exit opening was one boring of 1.5 mm diameter, i.e. a cross-section of 1.767 $mm^2$. It was found that this smaller exit opening resulted in irreproducible products from liquid compositions containing native conformation prion protein with aggregated conformation prion protein. Currently, it is assumed that the smaller exit opening results in shear forces which are generated in addition to the shear forces generated by the rotary element. Further, it was observed that in these devices, liquid composition was drawn into the bearing, allowing the bearing to exert additional shear forces onto the liquid.

Example 2

Production of Aggregated Conformation Prion Protein

As a first experiment, the starting liquid composition contained 5% vol/vol of the Protease K-resistant prion protein Sc237 BH, representing an aggregated conformation prion protein which is known to induce amplification of the aggregated conformation in the native conformation shNBH, was admixed with a 10% wt/vol preparation of hamster prion protein shNBH (Syrian hamster normal brain homogenate) having the native conformation, which was produced by homogenization of brain tissue detergent containing aqueous buffer solutions. From this stock, aliquots were each subjected to different shear force intensities using an array of the devices of Example 1 at cycles of 60 s shear force and 9 min resting phase without agitation for a total of 46 h in a thermostat at 37° C. to a shear force by rotation rates as indicated in FIG. 4 with an accuracy of 1 Hz. The rotary elements of the devices were introduced into 1.5 mL Eppendorf vials containing the liquid composition aliquots.

No deterioration of the precision of the shear force, i.e. no deviation of the control of rate of rotation was observed over the number cycles, indicating the reliability of the device.

For analysis of the amplification reactions, aliquots from each reaction were taken and digested with Proteinase K added to 50 μg/ml or 10 μg/ml, respectively. Samples were separated by SDS PAGE, detection was in a Western blot using anti-PrP antibody and Western Pico ECL solution (Pierce) for signal generation. The results are shown in FIG. 4, wherein the number of the tool identifies the individual device of the array, Hz indicates the rate of rotation used by the individual device, neg. denotes a 5% vol/vol dilution of 10% wt/vol Sc237 BH prion protein in 10% wt/vol shNBH, corresponding to the starting liquid composition, and ScBH, separated from neg. by an empty lane, denotes 10% wt/vol Sc237 BH prion protein digested at 50 μg/ml Proteinase K in each blot as a common positive control.

The Western blots show that the amount of Proteinase K resistant prion protein generated by amplification differs in dependence on shear force intensity, as indicated by the rates of rotation. Further, the comparison of samples generated at one shear force intensity but digested with different concentrations of Proteinase K indicates that the change in signal intensity differs between samples according to the shear force intensity. A quantitative analysis is shown in FIG. 5, wherein the signal intensities are shown after normalization to the positive control signal. In the graph, the shear force intensity is given as the speed of rotation (▲), each pair of columns gives Proteinase K resistant prion protein of the same rotation rate as indicated, with the left column indicating the signal intensity at 10 μg/ml Proteinase K, the right column indicating the signal intensity at 50 μg/ml Proteinase K. This analysis shows that in aliquots of one starting liquid composition of native conformation prion protein, amplification depends on the shear force intensity applied, e.g. different total concentrations of aggregated conformation prion protein is produced when using a different shear force intensity, e.g. generated by a speed of rotation differing by e.g. 10 or by 100 Hz.

This indicates that there is an optimum shear force intensity for amplification of the aggregated conformation of a prion protein.

A further effect of the different shear force intensities applied during amplification can be seen for the different Proteinase K concentrations, which show that the relative resistance against proteolysis differs between shear force intensities. This result indicates that the different shear force intensities result in different aggregated conformations of one prion protein during amplification.

Figure 6A:
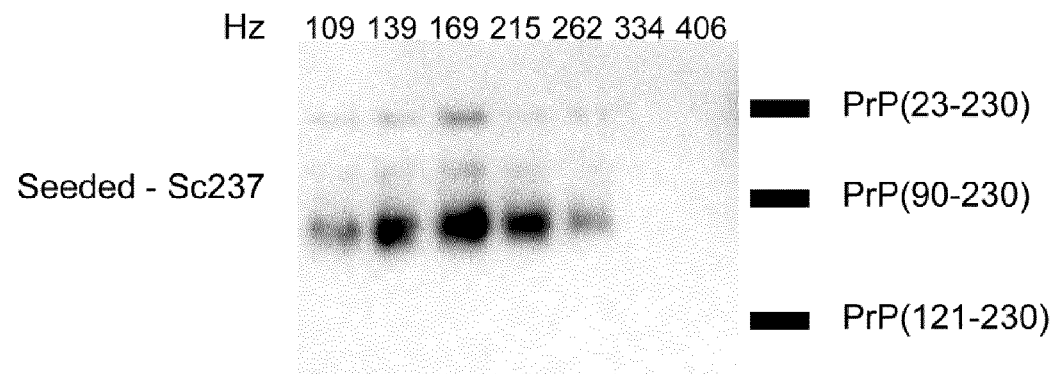
Figure 6B:
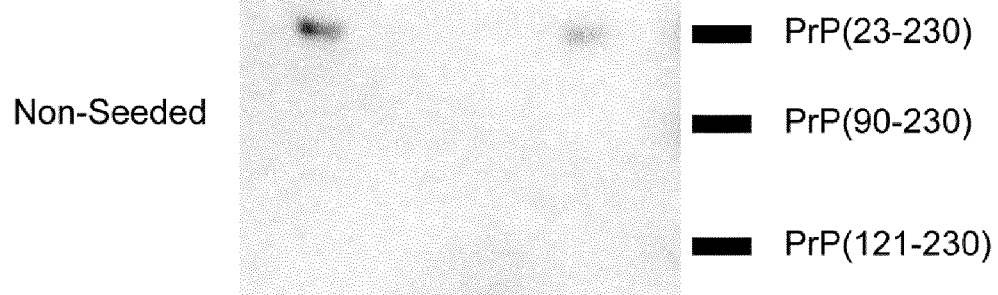

As a second experiment, 0.001 vol/vol of 10% wt/vol aggregated conformation Sc237 (hamster) prion protein was added to native conformation prion protein hamster PrP (amino acids 23-230) at 100 μg/ml to form a liquid composition for amplification using a total volume of 10 ml per reaction. For the process, 144 cycles of 60 s shear force and 9 min resting phase without agitation were performed at 37° C. An array of 7 devices as above was used, with the rotation rates controlled to 109 rpm to 406 Hz, controlled to a range of 1 Hz. Aliquots of samples were digested with 0.25 μg/ml Proteinase K at 37° C. for 30 min and analysed by SDS-PAGE and Western blotting. The result is shown in FIG. 6A, showing the Western blot for samples including Sc237 hamster prions, demonstrating amplification in a shear-force dependent manner. In FIGS. 6A and 6B, the individual rates of rotation generating the shear force intensity are indicated above lanes; markings to the right of the Western blots indicate expected positions of bands for the indicated prions. As shown in the Western blot of FIG. 6B, in the absence of Sc237 hamster prions, no proteinase K resistant band is observed, indicating that no amplification occurred in this aliquot.

FIG. 6 demonstrates that the amplification is strongly dependent on the shear rate, in the present example showing an optimum of 169 Hz, with the aggregated conformation prion protein PrP$^C$ at 0.25 μg/ml as a positive control.

Example 3

Analysis of Interaction of Test Compound on Amplification

Analysis of interaction of test compounds with prion protein that influences the amplification of aggregated conformation prion protein from native conformation prion protein was performed using aggregated prion protein produced according to Example 2 at one shear force intensity. A test compound was added at 6 μg/ml to 600 μg/ml to a liquid composition of 5% vol/vol Sc237 BH in 10% wt/vol native conformation hamster prion protein shNBH. Aliquots of the composition were subjected to 144 cycles of 60 s shear force and 9 min resting phase without agitation at 37° C. An array of 12 devices as above was used, with the rotation rates controlled to 1000 rpm to 16000 rpm, controlled to a range of 1 Hz. Aliquots of samples were digested with 5 to 50 μg/ml Proteinase K at 37° C. for 30 min and analysed by SDS-PAGE and Western blotting.

Example 4

Production of Distinct Aggregated Conformation Prion Protein Using Different Shear-Force Intensities Using an admixture of aggregated conformation Sc237 prion protein and a 10% preparation of normal hamster brain extract, aliquots were subjected to different shear-forces using the array of devices of Example 1. Shear-forces were generated at the rotation speeds indicated in Hz, samples were taken at 0, 1, 3, 6, 12, and 22 h during amplification (cycles of 5 s rotation, 5 min resting phase) as indicated.

FIG. 7 shows sections of the Western Blots of the immunologically detected amounts of proteinase K-resistant, i.e. aggregated conformation prion protein. Proteinase K digestion was at 50 μg/mL for 1 h at 37° C., followed by SDS-PAGE and Western Blotting. The progress of the amplification can be seen as the increase in intensities of aggregated conformation prion protein for each shear-force (Hz). The graphic analysis of the relative amount of aggregated conformation prion protein as derived from the Western Blot analysis is shown in FIG. 8 for each of the sampling periods. This analysis shows that amplification efficacy is dependent on the shear-force applied, in this experiment generating three distinct maximal amplification rates. FIG. 9 shows a graphic analysis of the kinetics of the amplification for those shear-forces (Hz) yielding maximum amplification.

These results show that the method produces a homogenous aggregated conformation prion protein at specific distinct shear-forces, because the efficacy and rate of the amplification are dependent on the intensity of the shear-force applied.

Example 5

Production of Homogenous Aggregated Conformation Prion Protein Using One Shear-Force Intensity For producing a preparation of aggregated conformation prion protein, Sc237 was admixed at 1/2500 with 50 μg/mL recombinantly produced and purified native conformation prion protein in a total reaction volume of 10.0 mL. For generating the shear-force, a rotating shear-force generator as described in Example 1 was rotated at 756 Hz at +/−1 Hz for 60 s with 540 s resting phase for 136 cycles. The comparative spontaneous amplification product was generated under the same processing conditions but with no aggregated prion protein added to the initial reaction, i.e. without Sc237 as a seeding agglomerated conformation prion protein.

Figure 10:
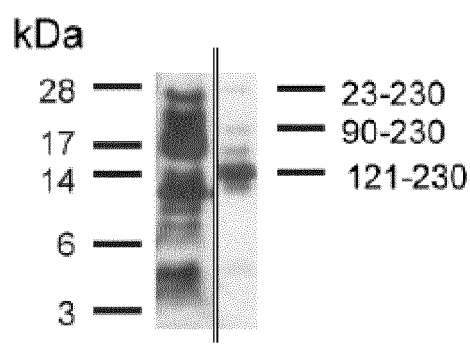

FIG. 10 shows an SDS-PAGE (silver stained) of the initial admixture of Sc237 with the native conformation prion protein (left lane) and of the produced aggregated conformation product. To the left, marker protein sizes are given in kDa, on the right, the migration patterns of three different PrP$^c$ (aggregated conformation prion protein) fragments are indicated. The increase in homogeneity of the protein in the reaction volume due to the shear-force applied is evident.

The produced aggregated conformation product was pelleted by centrifugation, yielding a total of 6 mg proteinase K-resistant protein when isolated. This protein, which following the production process is unperturbed, was used for solid-state $^{13}$C-NMR.

As a comparative sample, the product of spontaneous amplification (without initial aggregated prion protein) was used similarly for $^{13}$C-NMR.

Figure 11:
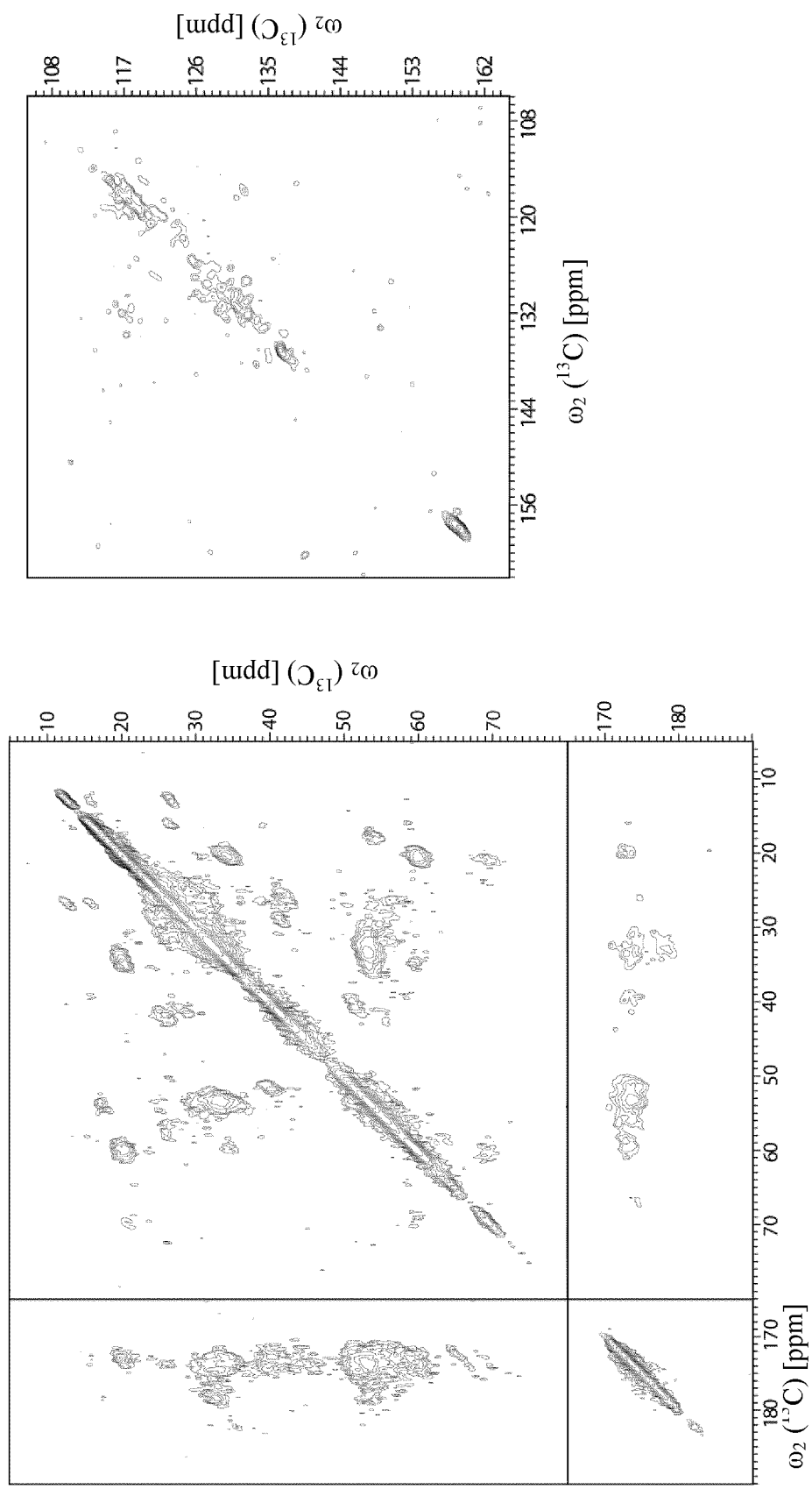

The CP-MAS NMR: $^{13}$C, $^{13}$C correlation is shown in FIG. 11 for the comparative spontaneous amplification product, and in FIG. 12 for the aggregated conformation product obtained by the process of the invention using controlled shear-force. The enlarged sections of the correlation graph show the upper right hand sections, namely the spectral region in which characteristic cross-peaks for isoleucine can be observed. In comparison to the spontaneous amplification product, the aggregated conformation product obtained by the process of the invention shows distinct signals for four of four isoleucine residues, indicating that this product predominantly consists of one conformation of aggregated prion protein, i.e. the distinct signals show a high homogeneity of the conformation of the product of the process of the invention. Further, the comparison of the enlarged section of the NMR spectrum of FIG. 12 shows enlarged peaks that correspond to $^{13}$C$^\beta$/$^{13}$C$^{\delta 1}$ and $^{13}$C$^\beta$/$^{13}$C$^{\gamma 2}$ atom pairs of individual amino acids. These results show that the chemical shifts depend on the shear force, as the product obtained at 756 Hz (Sc237-756 Hz) shows four paired isoleucine peaks, which differs from the product obtained at 189 Hz (Sc237-189 Hz) showing three paired isoleucine peaks and from the product of the comparative spontaneous agglomeration (Spont. 189 Hz) which shows at least eleven paired isoleucine peaks, indicating structural inhomogeneity.

Example 6

Analysis of a Mammalian Sample for Presence of Aggregated Conformation Prion Protein Analysis of the presence of aggregated conformation, i.e. disease-associated prion protein in a mammal was done using serial dilutions of 5% vol/vol Sc237 BH. The sample dilution was added to 10% wt/vol native conformation hamster prion protein, e.g. shNBH. Aliquots of the composition were subjected to 144 cycles of 60 s shear force and 9 min resting phase without agitation at 37° C. An array of 12 devices as above was used, with the rotation rates controlled to 1000 rpm to 16000 rpm, controlled to a range of 1 Hz. Aliquots of samples were digested with 5 to 50 μg/ml Proteinase K at 37° C. for 30 min and analysed by SDS-PAGE and Western blotting.

Example 6

Device for Controlled Shear-Force Generation Using Sonotrode

This Example shows a currently preferred embodiment of a device for application of controlled shear-force to the inner volume of reaction vessels using ultrasound.

As shown in FIG. 13, the surface 40 of a sonotrode 40 forms the bottom wall of a transfer liquid bath. Side walls 42 of the transfer liquid bath are arranged in a fluid-proof manner to the sonotrode 41, e.g. by sealing spacers 43. The transfer liquid bath is adapted to provide a thickness of the transfer liquid corresponding to the wave-length of the resonance frequency of the sonotrode 41 by the side walls 42 extending to the wave-length of the resonance frequency of the sonotrode 41 in perpendicular to the sonotrode surface 40. Accordingly, the transfer liquid level is pre-set by the side-walls 42 when filling the bath with transfer liquid, e.g. using filling pipe 44. Preferably, the device has an exit 45 for transfer liquid passing over the rim of side walls 42. The sonotrode 41 is coupled to a drive and converter unit 46. Reaction vessels 31 are each positioned at a distance to the sonotrode surface 40. The reaction vessels are each held in a clamping device 50 of a holder 51 that preferably is part of a controlled positioning device, which preferably is computer-controlled, e.g. having servo-drives for accurately positioning vessels 31. As depicted, in a simple embodiment for positioning vessels 31, the holders 51 are guided, e.g. in a threaded bore 53 provided at a distance over the transfer liquid and at a spacing from the sonotrode 41. The threaded bore can e.g. be arranged in a cover 54 over the transfer liquid bath. Cover 54 preferably is vibrationally decoupled from the sonotrode 41 and side walls 42, e.g. by arranging cover 54 on a support which is spaced from the sonotrode 41 and from the side walls 42.

The arrangement of holder 51 in a guiding bore 53 allows to accurately and repeatedly position the vessel 31 in relation to the shear-force generator, in this embodiment represented by the sonotrode 41.

FIG. 14 in greater detail shows that each reaction vessel 31 is held in a clamping means 50 that is mounted on a holder 51. The reaction vessel 31 contains an inner abutment face 52, against which the reaction vessel 31 is located for providing a reproducible position of the reaction vessel 31 at each holder 50. Preferably, the holder 51 is part of a computer-controlled positioning device, e.g. a robotic arm.

Reference numeral list:

| | |
|---|---|
| 1 | rotary element |
| 2 | axle |
| 3 | first bearing |
| 4 | second bearing |
| 5 | vessel |
| 6 | boring |
| 7 | holder |
| 8 | lid |
| 10 | first element of coupling |
| 11 | drive |
| 12 | second element of coupling |
| 13 | control unit |
| 14 | sensor |
| 20 | tube |
| 21 | exit opening |
| 22 | polymer tube |
| 23 | shoulder |
| 24 | sleeve |
| 25 | inner shoulder |
| 30 | housing |
| 31 | vessel |
| 40 | sonotrode surface, sonicator surface |
| 41 | sonotrode, sonicator |
| 42 | side wall |
| 43 | spacer |
| 44 | filling pipe |
| 45 | exit for transfer liquid |
| 46 | drive and converter unit |
| 50 | clamping means |
| 51 | holder |
| 52 | abutment face |
| 53 | threaded bore |
| 54 | cover |

The invention claimed is:

1. A process for amplification of aggregated conformation prion protein from native conformation prion protein, comprising:
   contacting the native conformation prion protein with the aggregated conformation prion protein in a liquid to form a liquid composition; and
   subjecting the liquid composition to at least one cycle comprising the generation of shear force for fragmenting the aggregated conformation prion protein and a resting phase,
   wherein the shear force is applied to each volume element of the liquid composition and consists of a uniform shear-force intensity having a value within ±10% of a given shear-force value,
   wherein the shear-force is generated by rotation of a rotary element arranged within a spaced coaxial wall and passing each volume element between the rotary element and the wall while the rotation is controlled to within ±10% of one rate.

2. The process according to claim 1, wherein the wall is a wall section of circular cross-section of a vessel containing the liquid composition, and the rotary element rotates on an axle that is coaxially arranged within the wall section of the vessel.

3. The process according to claim 1, wherein the wall is an inner wall of a tube and the tube is fixed to a sleeve containing a bearing in which an axle attached to the rotary element rotates and each volume element passes between the rotary element and the tube while the rotation is controlled to within ±10% of the one rate and each volume element exits through at least one exit opening arranged between the tube and the sleeve, the exit opening having a cross-section of at least the cross-section between the rotary element and the tube.

4. The process according to claim 1 applied to analysis of a sample originating from a mammal, wherein the sample contains the aggregated conformation prion protein and that following the application of shear force, an increase in aggregated conformation prion protein is detected.

5. The process according to claim 1, wherein at least two aliquots are taken from the liquid composition, which aliquots are concurrently applied with the same or each one different shear-force of uniform intensity.

6. The process according to claim 5, wherein a compound is added the first aliquot of the at least two aliquots, a second aliquot of the at least two aliquots remains without addition of the compound, and that following the application of shear-force, a change of the aggregated conformation prion protein in the first aliquot is detected in relation to the aggregated conformation prion protein in the second aliquot.

* * * * *